United States Patent [19]

Downing

[11] Patent Number: 4,821,715
[45] Date of Patent: Apr. 18, 1989

[54] NASOPHARYNGEAL AIRWAY

[76] Inventor: Michael V. Downing, 3520 Myrtle Ave., Covington, Ky. 41015

[21] Appl. No.: 155,912

[22] Filed: Feb. 16, 1988

[51] Int. Cl.<sup>4</sup> ............... A61M 15/08; A62B 9/04; A62B 7/02

[52] U.S. Cl. ............... 128/207.18; 128/203.22; 128/200.26

[58] Field of Search ............... 128/911, 207.17, 207.18, 128/203.22, 202.27, 200.26; 604/256, 258

[56] References Cited

U.S. PATENT DOCUMENTS

| | | | |
|---|---|---|---|
| 2,230,218 | 2/1941 | Asche | 604/43 |
| 3,260,258 | 7/1966 | Berman | 128/207.18 |
| 3,495,595 | 2/1970 | Soper | 604/28 |
| 3,568,678 | 3/1971 | Pourquier | 128/348 |
| 3,802,431 | 4/1974 | Farr | 128/207.18 |
| 3,814,103 | 6/1974 | Fettel et al. | 128/207.18 |
| 3,876,946 | 2/1975 | Huddy | 128/207.18 |
| 3,915,173 | 10/1975 | Brekke | 128/207.18 |
| 3,999,554 | 12/1976 | Kim et al. | 128/350 |
| 4,022,219 | 5/1977 | Basta | 128/351 |
| 4,054,135 | 10/1977 | Berman | 128/208 |
| 4,150,676 | 4/1979 | Jackson | 128/207.18 |
| 4,280,493 | 7/1981 | Council | 128/207.18 |
| 4,300,550 | 11/1981 | Gandi et al. | 128/207.18 |
| 4,332,242 | 6/1982 | Chikama | 128/3 |
| 4,338,930 | 7/1982 | Williams | 128/200.26 |
| 4,363,323 | 12/1982 | Geiss | 604/281 |
| 4,405,313 | 9/1983 | Sisley et al. | 604/43 |
| 4,406,656 | 9/1983 | Hattler et al. | 604/280 |
| 4,540,402 | 9/1985 | Aigner | 604/44 |
| 4,699,139 | 10/1987 | Marshall et al. | 128/207.18 |

Primary Examiner—Edgar S. Burr
Assistant Examiner—Kimberly L. Asher
Attorney, Agent, or Firm—Wood, Herron & Evans

[57] ABSTRACT

An improved nasopharyngeal airway simultaneously maintains patency of the breathing passage while providing continuous oxygenation to the back of the oropharynx region of a conscious or unconscious patient through at least one unobstructed integral lumen extending the length of and adjacent the airway. Additional medical procedures can be performed through the airway during constant oxygenation without discontinuous or reducing oxygenation and without causing tissue trauma which would otherwise occur but for the guidance and protection of the airway.

9 Claims, 1 Drawing Sheet

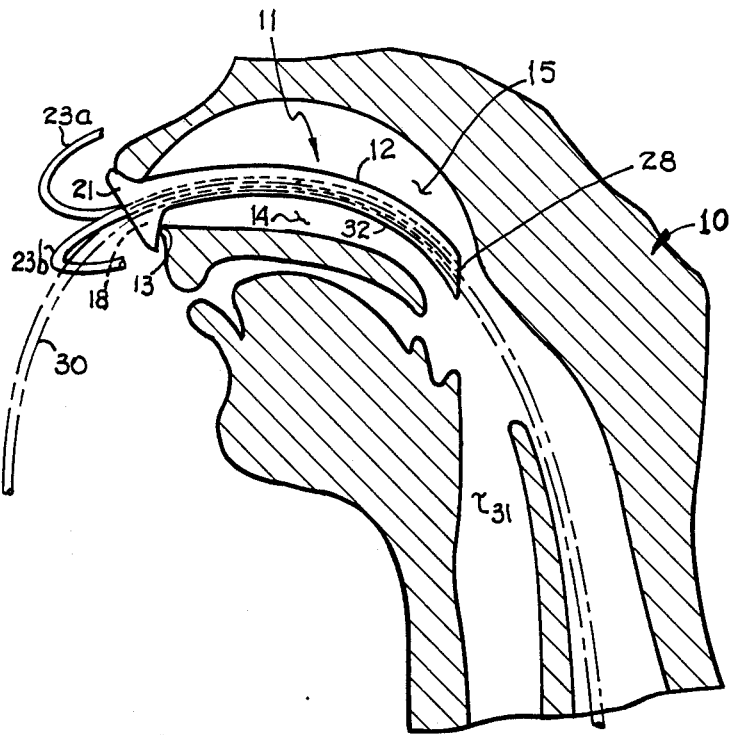
FIG. 2
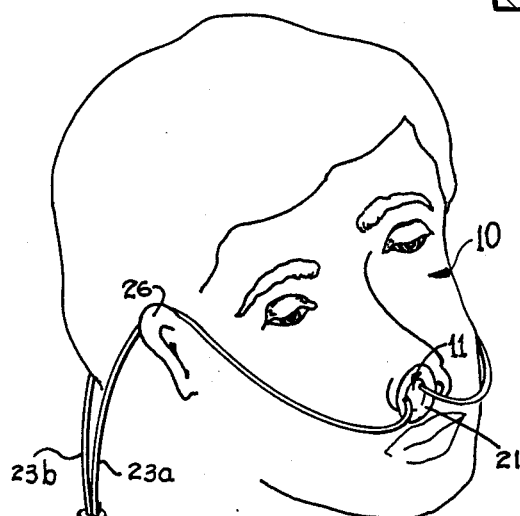
FIG. 1
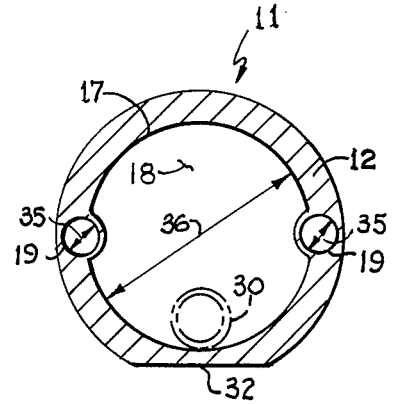
FIG. 3
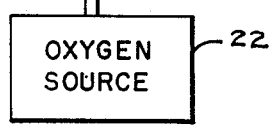

NASOPHARYNGEAL AIRWAY

FIELD OF THE INVENTION

This invention relates to a nasopharyngeal airway, and more particularly to an improved nasopharyngeal airway which facilitates the constant, effective delivery of oxygen to a patient.

BACKGROUND OF THE INVENTION

Typical nasopharyngeal airways constitute a tubular airway inserted through a nostril of a patient for extension through the nasal passge to the back of the oropharynx region in order to maintain the patency of the breathing passage. Such an airway is typically about 4"–6" long and is made of a pliable synthetic material. A flange at the nasal end holds the airway in place relative to the nasal passage.

Such nasopharyngeal airways can be used during surgery, or during other periods of time when it is desirable to insure against collapse of the breathing passage. When the airway is required to be kept in place for an extended length of time, a smaller tube or tubes may be projected through the airway for the purpose of providing gastric treatment, feeding or decompression, for example. Such tubes severely restrict the cross-sectional flow area of the airway.

Typical nasopharyngeal airways do not provide for adequate oxygenation of a patient during certain medical procedures requiring insertion of tubes into the body through the nasal passage. Although a tube could be extended through the airway in order to administer oxygen, in much the same manner as described above for gastric treatment, the cross sectional dimension of the airway is limited, and use of an oxygen tube extended through the airway takes up space that could otherwise be used for administering other treatment. Moreover, some space must remain open through the length of the airway in order to allow the patient to exhale, and maybe to inhale as well, if oxygenation is used only to supplement the normal breathing.

Certain medical conditions require aspiration of fluids from the bronchial/tracheal region of the patient by applying suction through a tube extending through the nasal passage. Other medical apparatus than airways of the foregoing type have been used to suction or otherwise treat a patient and supply oxygen but have numerous disadvantages. For example, Gandi U.S. Pat. No. 4,300,550 discloses a dual passage suction catheter which is inserted through the nasal passage of the patient and extended into the tracheal passage for use in aspirating a patient. The catheter permits delivery of oxygen at a critical time to the tracheal area, well below the oropharynx, of a patient to be oxygenated. Simultaneously, the catheter also permits an aspiration procedure requiring the suction end of the catheter in the tracheal area. After suction and oxygenation is completed, typically for about one minute, the catheter is removed from the patient and discarded.

Sometimes patients require oxygenation over an extended period of time. While the unconscious patient may not exhibit gag reflexes, the catheter of Gandi would cause gagging in a conscious patient and thus cannot be continuously used. The requirement to provide constant oxygenation precludes use of a tracheal tube of the type disclosed by Gandi. Moreover, frequent insertion of such a dual catheter to provide oxygenation and suction can cause multiple trauma and swelling to the throat and nasal passage tissues.

It is thus an objective of the invention to provide an improved airway which facilitates constant patient oxygenation yet provides channels for other medical procedure and apparatus without interfering with oxygen delivery.

It is another object of this invention to provide a device which simultaneously accommodates constant oxygenation and maintains patency of the breathing passage of a conscious or unconscious patient in a manner which does not cause gagging or induce the cough reflex.

It is a still further object of this invention to provide a device which accommodates constant, continuous oxygenation, maintains patency of the breathing passage of a conscious or unconscious patient, and prevents tissue trauma caused by insertion of additional treatment apparatus through the nasal passage.

SUMMARY OF THE INVENTION

To these ends, a prefered embodiment of the invention includes a tube defining within its walls an airway passage of predetermined length, and preferably two unobstructed lumens formed integrally within a wall of the tube and extending the length of and adjacent the airway passage. Each lumen communicates with an extended flexible oxygen tube connected to an oxygen source, thereby allowing oxygen to be supplied continuously to the back of the oropharynx of a patient when the airway is in place. Preferably, the oxygen tubes are of sufficient length to be looped behind the ears of the patient during constant oxygenation, thus providing a harness for the airway which does not require tape or other fastening means. By looping the tubes away from the nasal end of the inserted airway, the harness also facilitates access to the airway for other medical purposes.

The nasopharyngeal airway of this invention can remain in place over extended periods of time to maintain the patency of the breathing passage while providing constant oxygenation. Because the lumens are formed within the walls of the airway, constant oxygenation can be provided without taking up space inside the airway which is needed for normal inhaling and exhaling. Moreover, because the inserted airway extends only to the oropharynx, use of the airway does not induce gagging or coughing in either a conscious or unconscious patient. It alleviates tissue trauma associated with repeated insertion of other devices such as oxygen or suction tubes, and facilitates the simultaneous administration of at least one other medical procedure which may be required without interfering with constant oxygenation of the patient.

These and other objects and advantages will be further appreciated from the following detailed description of a preferred embodiment and from the drawings in which:

BRIEF DESCRIPTION OF THE DRAWINGS

FIG. 1 is a diagrammatic view of a portion of the nasopharyngeal airway of this invention, operably disposed in a patient;

FIG. 2 is a cross-sectional view of the nasopharyngeal airway of this invention residing within a patient and showing in phantom an additional treatment device extending through the airway; and FIG. 3 is a transverse cross-sectional view of a preferred embodiment of the nasopharyngeal airway of this invention, showing in phantom an additional tube extending through the airway.

DETAILED DESCRIPTION OF THE DRAWINGS

Constant oxygenation can be provided to a patient 10 with the nasopharyngeal airway 11 of this invention, shown in FIGS. 1, 2 and 3. The airway 11 comprises a tube 12 of predetermined length which, when inserted through the nares 13, extends through the nasal passage 14 to the oropharynx 15 of the patient 10. The tube 12 has an inside wall 17 which defines an airway passage 18, shown in FIG. 3. At least one, but preferably two, unobstructed lumens 19 are formed within the inside wall 17 of the tube 12. Each lumen 19 extends the length of and is adjacent to the airway passage 18. Preferably, the lumens 17 are integrally formed within the airway 11, and along with tube 12, are molded as one piece. At an outer end 21 of airway 11, the lumens 19 are operatively connected to an oxygen source 22 via at least one and preferably two, oxygen tubes 23a and 23b. Preferably, with the airway 11 inserted, oxygen tubes 23a and 23b are of sufficient length to be routed around the ears 26 of the patient 10 to provide harness means as shown in FIG. 1. Use of the harness alleviates the need to tape the airway 11 to the patient 10 and further facilitates access to the airway passage 18 for other medical purposes. Preferably, the oxygen tubes 23a and 23b are molded with the airway 11.

FIG. 2 shows the airway 11 residing within a patient 10, with outer end 21 protruding from the nares 13 and an inner end 28 residing in the back of the oropharynx region 15. Preferably, outer end 21 is flanged to maintain the relative position of the airway 11 in the nasal passage 14.

An additional tube 30, shown in FIGS. 2 and 3, projects through the airway 11 for the purpose of simultaneously administering an additional medical procedure such as gastric feeding or decompression, during constant oxygenation. Alternatively, or additionally, such tubes can also be used to aspirate the patient 10 while constant oxygenation is provided. For the purpose of providing aspiration, the tube 30 would not be extended as far as that shown in FIG. 2, but would reside nearer to the trachea region 31 of the patient 10.

In a preferred embodiment, as shown in FIG. 3, a wall 17 of the airway 11 comprises a wall of each lumen 19. Each lumen 19 has an inside diameter 35, which is small relative to an inside diameter 36 of the airway 11. About midway between the two lumens 19, an outer lower surface 32 of the airway 11 has a flattened portion to better facilitate insertion and continued proper disposition of the airway 11 in the nasal passage 14 of the patient 10. The combination of the flange at outer end 21, shown in FIGS. 1 and 2, and the harnessing of the oxygen tubes 23a and 23b also insures secured placement of the airway 11 to the patient 10, while facilitating ready access to the passage 18 for administering additional medical procedures.

With the airway 11 inserted in the patient 10, patency of the breathing passage 14 is maintained while constant oxygenation is provided. This is done in a manner which facilitates the simultaneous administering of at least one additional medical procedure. Because constant oxygenation is provided through at least one lumen 19 extending within the wall 17 of the airway 11, there is no need to take up space in the passage 18 with an oxygen tube projected through the airway 11. Thus, this invention facilitates constant patient oxygenation, yet provides a relatively large, unobstructed airway passage 18 for other medical procedures and apparatus without interfering with oxygen delivery.

The airway 11 can be left in place for extended periods of time, as perhaps required during a lengthy surgical procedure or stay in intensive care, without inducing reflex coughing or gagging of the patient. Constant oxygenation can be delivered to the back of the oropharynx through the lumen while the airway 11 remains in place for as long as a week or ten days. By providing constant oxygenation through a nasopharyngeal airway 11 that is maintained in the patient 10, trauma to the nasal passage 14 caused by repeated insertion of oxygen tubes is alleviated.

While the above description constitutes a preferred embodiment of the nasopharyngeal airway of this invention, it is to be understood that the invention is not limited thereby and that in light of the present disclosure of the invention, various other alternative embodiments will be apparent to a person skilled in the art. Accordingly, it is to be understood that changes may be made without departing from the scope of the invention as particularly set out and claimed.

I claim:

1. An improved nasopharyngeal airway comprising:
    a tube having a predetermined length from end to end which extends from the tip of the nares to the oropharynx of a patient and in all cases short of the trachea and the esophagus of said patient when inserted completely into a nasal passage, said tube defining an airway passage having an open end located proximate a distal end of said tube;
    at least one unobstructed lumen completely enclosed in a wall of said tube and extending the length of said tube adjacent said airway passage, said lumen having an open end proximate the distal end of said tube;
    means for operably connecting said lumen to a source of oxygen;
    wherein said airway passage is unobstructed and provides a channel for insertion of medical apparatus for patient treatment while oxygen is simultaneously delivered to the oropharynx of a patient through said at least one lumen, and said airway defining a medical apparatus guide for preventing tissue damage which may otherwise result from frequent insertion and withdrawal of such other medical apparatus.

2. An improved nasopharyngeal airway as in claim 1 wherein said lumen is integrally formed within a wall of said airway.

3. An improved nasopharyngeal airway as in claim 1 and further comprising:
    two unobstructed lumens completely enclosed in a wall of said tube and extending the length of said tube adjacent said airway, each of said lumens having an opening proximate the distal end of said tube, and said lumens being located on opposite sides of said airway;
    means operatively connecting said two unobstructed lumens to said oxygen source.

4. An improved nasopharyngeal airway as in claim 3 wherein said operatively connecting means further comprises:

two oxygen tubes constituting harness means for securing said improved airway to said patient during the delivery of constant oxygenation.

5. An improved nasopharyngeal airway as in claim 1 wherein said tube includes a flat portion running along the lower length thereof to facilitate insertion and continued disposition of the improved airway in the nasal passage of the patient.

6. An improved nasopharyngeal airway as in claim 1 wherein said airway has a first end for residing outside the nasal passage and a second end for residing in the back of the pharyngeal region when said airway is completely inserted into said patient, and further comprising:
a flange at said first end to prevent said second end from extending beyond said pharyngeal region during said constant oxygenation.

7. An improved nasopharyngeal airway comprising:
a tube having a predetermined length from end to end which extends from the tip of the nares to the oropharynx of a patient and in all cases short of the trachea and the esophagus of said patient when inserted completely into a nasal passage, said tube defining an airway passage having an open end located proximate a distal end of said tube;
two unobstructed lumens completely enclosed in a wall of said tube and extending the length of said tube adjacent said airway passage, each of said lumens having an opening proximate the open end of said tube;
means operably connecting said lumens to a source of oxygen, said connecting means further comprising oxygen tubes defining a harness for securing said improved airway to said patient;
wherein said airway passage is unobstructed and provides a channel for insertion of medical apparatus for patient treatment while oxygen is simultaneously delivered to the oropharynx of a patient through said lumens, said airway defining a medical apparatus guide for preventing tissue damage which may otherwise result from frequent insertion and withdrawal of such other medical apparatus.

8. A method of providing continuous oxygenation to a conscious or unconscious patient comprising the steps of:
inserting said tube from the tip of the providing a tube having a predetermined length from end to end which extends from the tip of the nares to the oropharynx of a patient and in all cases short of the trachea and the esophagus of said patient when inserted into a nasal passage, said tube defining an airway passage having an open end located proximate a distal end of said tube, said tube having at least one unobstructed lumen completely enclosed within a wall thereof, said at least one lumen extending the length of said tube adjacent to said airway passage and having an open end proximate the distal end of said tube;
inserting said tube from the tip of the nares to the oropharynx region of a patient; and
maintaining the patency of the breathing passage of a patient with said tube; and
delivering oxygen constantly to the back of the oropharynx region of the patient through said lumen.

9. A method of providing oxygenation to a conscious or unconscious patient as in claim 8 and further comprising the step of:
extending a medical apparatus through said airway passage into a patient;
administering through said medical apparatus extended through said airway passage at least one additional medical procedure to said patient during said oxygen delivering step.

* * * * *

UNITED STATES PATENT AND TRADEMARK OFFICE
CERTIFICATE OF CORRECTION

PATENT NO. : 4,821,715
DATED : April 18, 1989
INVENTOR(S) : Michael V. Downing

It is certified that error appears in the above-identified patent and that said Letters Patent is hereby corrected as shown below:

Column 6, line 9, delete "inserting said tube from the tip of the"

Signed and Sealed this

Twentieth Day of February, 1990

Attest:

JEFFREY M. SAMUELS

Attesting Officer — Acting Commissioner of Patents and Trademarks